United States Patent [19]

Orr

[11] Patent Number: 4,949,714

[45] Date of Patent: Aug. 21, 1990

[54] SCAVENGING MEDICAL HOOD

[75] Inventor: Robert L. Orr, San Clemente, Calif.

[73] Assignee: Viratek Inc., Costa Mesa, Calif.

[21] Appl. No.: 385,892

[22] Filed: Jul. 26, 1989

[51] Int. Cl.⁵ ............................................. A61M 16/00
[52] U.S. Cl. ........................... 128/200.24; 128/205.19;
128/205.26; 128/910
[58] Field of Search ...................... 128/200.24, 201.23,
128/201.25, 202.12, 205.26, 205.27, 205.28,
205.29, 205.12, 205.15, 205.19, 909, 910

[56] References Cited

U.S. PATENT DOCUMENTS

| | | | |
|---|---|---|---|
| 2,130,718 | 9/1938 | Fujita | 128/205.28 |
| 2,418,473 | 4/1947 | Lambersten et al. | |
| 2,891,542 | 6/1959 | Pentecost | |
| 3,610,716 | 10/1971 | Weinberg et al. | 312/236 |
| 3,680,557 | 8/1972 | Doniguian | 128/205.26 |
| 3,889,670 | 6/1975 | Loveland et al. | 128/204 |
| 3,903,869 | 9/1975 | Bancalari | 128/202.12 |
| 4,003,378 | 1/1977 | Pickering | 128/204 |
| 4,055,173 | 10/1977 | Knab | 128/139 |
| 4,161,172 | 7/1979 | Pickering | 128/205.26 |
| 4,727,871 | 1/1985 | Smargiassi et al. | 128/204.17 |
| 4,739,753 | 4/1988 | Brehm | 128/200.24 |
| 4,763,664 | 8/1988 | Merilainen | 128/718 |
| 4,832,042 | 5/1989 | Poppendiek et al. | 128/205.19 |
| 4,881,553 | 11/1989 | Angell | 128/201.25 |

FOREIGN PATENT DOCUMENTS 3536519 4/1987 Fed. Rep. of
Germany ..................... 128/200.24
29119 of 1912 United Kingdom ........... 128/205.26

Primary Examiner—Eugene H. Eickhoft
Attorney, Agent, or Firm—Herb Boswell

[57] ABSTRACT

A scavenging medical hood includes a hood for fitting over the head of a patient. A gas inlet port leads to the interior of the hood for supplying the interior of the hood with an appropriate respiratory gas and an aerosolized medicinal agent contained within that respiratory gas. A gas outlet connects between the interior of the hood and the ambient air for discharge of gas from the interior of the hood including any residual aerosolized medicinal agent remaining in that discharged gas. A vacuum port is located adjacent to the gas outlet. A vacuum is applied to the vacuum port via a suitable motorized vacuum source. Vacuum at the vacuum port aspirates gas from the area of the gas outlet to aspirate respiratory gas, residual aerosolized medicinal agent still suspended in the respiratory gas and ambient air from the vicinity of the gas outlet into the vacuum port. A filter located in the vacuum line serves to filter out the residual aerosolized medicinal agent from the aspirate in the gas line.

23 Claims, 3 Drawing Sheets

SCAVENGING MEDICAL HOOD

BACKGROUND OF INVENTION

This invention is directed to a scavenging medical hood for removal of residual aerosolized medicinal agent from respiratory gas passed through the hood.

A variety of medicinal agents are administered as aerosol sprays to patients in need thereof. Generation of the aerosol spray is accomplished via one of many commercially available nebulizers.

For adults and older children hand held nebulizers are used for short term or single dose therapy of an aerosolized medicinal agent. These hand devices are not suitable for use with small children or infants since they require cooperative breathing of the patient.

Aside from intubation, if long term administration of an aerosolized medicinal agent is necessary, or if it is necessary to administer a medicinal agent to a severely compromised adult or older child as, for instance, a comatosed patient, and in all instances for administration to young children and infants, administration is accomplished utilizing a hood or tent.

Various hoods and tents (oxygen tents) are commercially available for the administration of oxygen and other respiratory gasses to patients in need thereof. A typical hood or tent utilized as an enclosure for respiratory therapy has to accommodate a patient who normally is in a prone position in a bed, crib or the like. The enclosure must therefore seal against normal bedding, as for instance, sheets, blankets and pillows. Inherently these seals are not imperforate. Aside from spark and flame arrestment, during normal oxygen therapy this does not present any problems since leakage at such imperfect seals only constitutes enrichment of the oxygen in the ambient atmosphere around the outside of the enclosure.

Respiration involves the exchange by the patient of carbon dioxide for oxygen. Because of biological feedback mechanisms wherein the concentration of the carbon dioxide affects the breathing of the patient it is necessary to purge carbon dioxide from the respiratory gasses inhaled by the patient. This, thus requires a continuous flow of respiratory gas into a suitable hood or tent with the volume of the input gas sufficient to essentially flush the respiratory environment within the hood or tent of carbon dioxide. Normally a positive gas flow is established through the hood or tent with the excess gas flow discharged directly to the ambient environment.

An aerosolized medicinal agent can be administered via a hood or tent by simply introducing the output of a nebulizer into the input gas stream of the hood or tent. In a simplistic sense the humidification of oxygen gas fed to an oxygen tent can be considered as such a system. In this case the water vapor introduced to the oxygen stream could be equated as a medicinal agent serving to the humidify the air for facilitation of respiration of the patient. As with the discharge of oxygen, discharge of excess water vapor to the ambient air whether via an outlet port of the tent or via leakage from imperfect seals does not constitute an environmental problem.

When medicinal agents are added to the respiratory gasses of a hood or tent, sufficient medicinal agent must be added to the gasses to account for the continuous flushing of excess gas through the hood or tent. In the water vapor example discussed above, excess medicinal agent discharged from a tent or hood, i.e. the water vapor, is completely benign once it is exhausted from the hood or tent. In other cases, however, it is desirable not to vent excess medicinal agent to the ambient environment external of the hood or tent.

Attempts have been made to purge tents or hoods of excess medicinal agent. The basic premise of all of these attempts is the connection of a vacuum system directly to the interior of the hood or tent. The vacuum system is then used to remove gas containing excess or residual medicinal agent prior to the expulsion of the same to the ambient environment.

The use of such direct vacuum removal of excess or residual medicinal agent from the interior of a respiratory device such as a hood or tent, has only been marginally successful. This is because equilibrium must be established and maintained between the flow rate of gasses into the enclosure against the vacuum exhaust of gasses from the enclosure.

Establishing and maintaining gas flow equilibrium is difficult. If there is a net positive pressure within the interior of the enclosure, i.e. the flow rate into the hood or tent is greater than the vacuum flow rate out, excess gas and medicinal agent contained therein will leak from the enclosure, as for instance, around bed sheets, draped seams and the like. If there is a net negative pressure, i.e. the vacuum flow rate is greater than the respiratory gas input flow rate, the concentration of the respiratory gasses and/or the medicinal agent suspended therein will be diluted by ambient air which will be drawn into the enclosure through the very same inefficient seals around bed sheets, draped seams and the like. Even when equilibrium is established if, for instance, the patient moves disturbing the seal of the enclosure against beds, sheets, pillows or the like, the equilibrium can be disrupted.

Thus, to establish and maintain equilibrium in a vacuum removal system either very complex and thus very expensive monitoring equipment must be utilized or constant attention by medical personnel is required to continuously adjust the flow rates.

BRIEF DESCRIPTION OF THE INVENTION

In view of the above, it is evident there exists a need for new and improved scavenging devices for utilization with medical hoods for removal of residual medicinal agent from respiratory gasses exhausted from the medicinal hood. Further, it is evident that there exists a need for such devices which are simple in construction and operation and therefore do not require an armada of instrumentation, controls and the like for their operation. Further, it is evident that there exists a need for such devices which can be operated by medical personnel without either undue extended training and/or constant attention during operation of the device.

These and other objects as will be evident from the remainder of this specification can be achieved in a scavenging medical hood which includes a patient enclosure means for enclosing at least the head area of a patient. The patient enclosure means has a hollow interior which is sized and shaped to contain at least the head of the patient surrounded by a volume of gas suitable for providing respiration gas to said patient. A gas inlet port means is connected to the enclosure means to supply both a respiratory gas and an aerosolized medicinal agent contained within the respiratory gas to the interior of the enclosure means. A gas outlet means is connected to the enclosure means for exhausting gas and residual aerosolized medicinal agent contained within such exhausted gas from the interior of said enclosure means. A vacuum port means for aspiration is located exterior of the enclosure means in operative association with the gas outlet means. The vacuum port means serves to aspirate gas, residual aerosolized medicinal agent within such gas and ambient air from the vicinity of the gas outlet means. A vacuum means for supplying an aspirate vacuum is connected to the vacuum port means for aspirating gas, residual aerosolized medicinal agent contained in such gas and ambient air from the vicinity of the gas outlet means.

The enclosure means can be constructed as a multi-sided hood which includes a patient opening having a patient collar means located therein. The patient collar means serves to passively seal against a body surface of the patient to inhibit gas flow adjacent to that body surface from the interior of the hood to the exterior of the hood.

Additionally, an air baffle means for passivating ambient air movements can be located on and extend away from the hood. The air baffle means is positioned in operative association with both the gas outlet means and the vacuum port means to at least partially shield the gas outlet means and its associated the vacuum port means from air currents in the ambient air.

Also, positioning of the gas outlet means in association with the patient opening allows for positioning of the air baffle means around the gas outlet means, the vacuum port means and the patient opening for scavenging gasses exhausted both from the gas outlet means as well as any gas leakage which might occur adjacent to the surface of the patient.

Further, the objects of the invention are achieved in a scavenging medical hood which includes a multi-sided hood having an interior. A gas inlet port is located in one of the sides of the hood, a patient opening is located in one of the sides of the hood and at least one gas outlet orifice is located in one of the sides of the hood. The gas outlet orifice extends between the interior of the hood and ambient air exterior of the hood. A vacuum port having a vacuum orifice is positioned adjacent to the gas outlet orifice whereby in response to gas movement through the vacuum gas orifice gas is aspirated from the ambient area immediately adjacent the gas outlet orifice. A motorized vacuum source and a filter are connected to the vacuum port for aspirating gas into the vacuum orifice with the filter positioned in the aspirated gas downstream from the vacuum orifice.

BRIEF DESCRIPTION OF THE DRAWINGS

This invention will be better understood when taken in conjunction with the drawings wherein.

This invention utilized certain principles and/or concepts as are set forth in the claims appended hereto. Those skilled in the medical device arts to which this invention pertains will realize that these principles and/or concepts are capable of being utilized in a variety of embodiments which may differ from the embodiment utilized for illustrative purposes herein. For this reason this invention is not to be construed as being limited solely to the illustrative embodiments, but should only be construed in view of the appended claims.

DETAILED DESCRIPTION OF THE INVENTION

Figure 1:
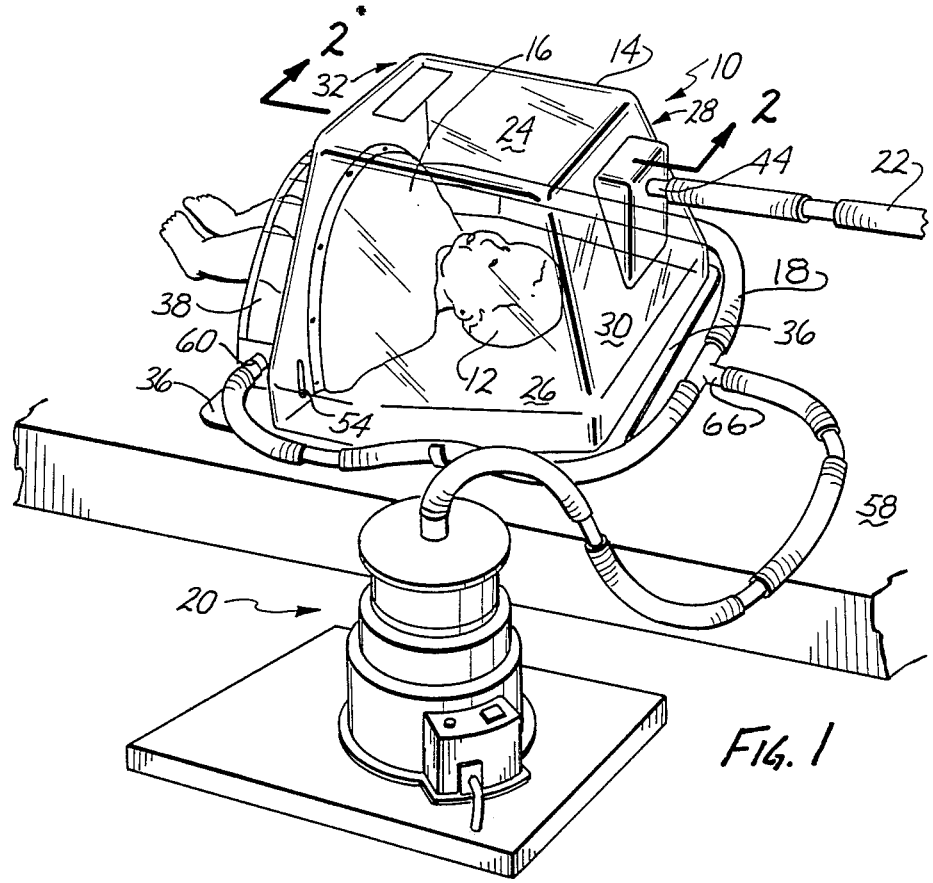
FIG. 1 is an isometric view of a scavenging medical hood of the invention and shows use of this scavenging medical hood with an infant patient.

FIG. 1 illustrates a scavenging medical hood 10 of the invention. As seen in FIG. 1 a patient 12, an infant, is undergoing respiratory therapy in conjunction with the hood 10 of the invention.

The scavenging medical hood 10 can be broken down into several major components. These include a patient enclosure means or multi-sided hood 14, a collar means or collar 16 attached to the hood 14 and a vacuum means consisting of vacuum tubing generally indicated with the numeral 18 and a vacuum and filter unit generally indicated at the numeral 20.

Not shown in FIG. 1 would be a suitable supply of respiratory breathing gas and a nebulizer for the introduction of an aerosolized medicinal agent into that respiratory gas. Such units are common and are commercially available. A suitable respiratory gas containing an aerosolized medicinal agent is introduced into the hood 14 via a gas inlet conduit 22.

Figure 2:
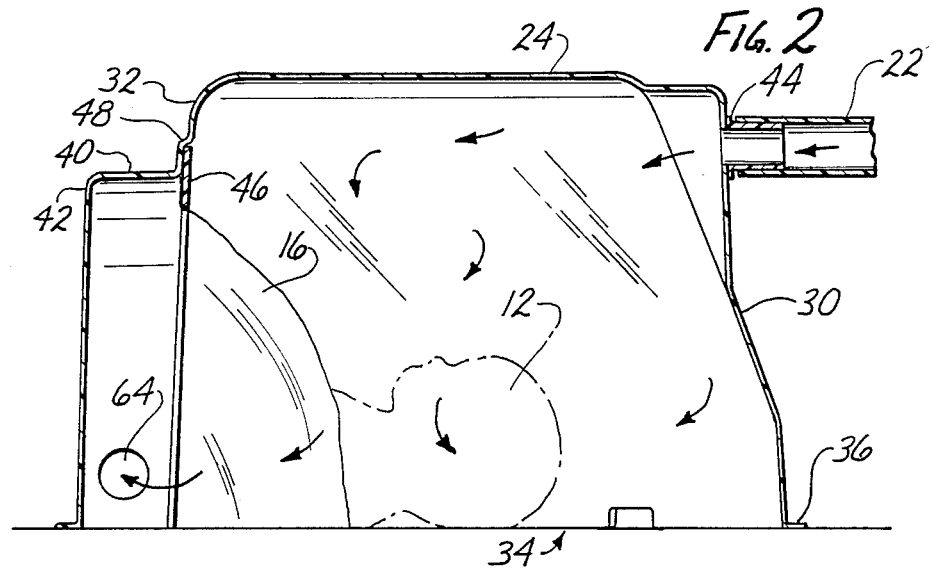
FIG. 2 is a cross sectional elevational view about the lines 2—2 of FIG. 1.

The hood 14 is composed of a top side 24, a right side 26, a left side 28, a back side 30, a front side 32, and an open bottom side 34 (see FIG. 2). A bottom flange 36 extends around the periphery of the bottom side 34.

An air baffle means or baffle 38 is integrally formed with the front side 32. The baffle 38 can be broken down into an arched shaped curving extensior 40 which has a flange 42 on its periphery distal from the wall 32 of the hood 14.

The hood 14, including its component sides 24, 26, 28, 30, and 32 (excluding the open bottom side 34, but including the bottom flange 36) as well as the baffle 38 are integrally formed from a single piece of material. Particularly preferred for use to form the hood 14 is a clear, transparent polysulfone plastic. Such material can be advantageously utilized within a hospital environment because it is impervious to detergents, can be disinfected with quaternary ammonium solutions, steam autoclaved (to about 274° F.) or disinfected with ethylene oxide gas.

Located near the top of the back side 30 is a gas inlet port 44 which together with the conduit 22 comprise a gas inlet port means. This serves as a connection for the inlet conduit 22 to supply respiratory gas or a respiratory gas containing an aerosolized medicinal agent to the interior of the hood 14.

An arched insert 46 is sonic welded to the inside of a curving shoulder 48 at the juncture of the extension 40 to the front wall 32. After sonic welding the arch insert 46 can thus be considered as being integral with the remainder of the hood 14. The arch insert 46 includes an arch shaped patient opening 50 centrally located in the insert 46.

A plurality of stainless steel male snaps 52 are symmetrically located about the patient opening 50. The patient collar 16 includes a like plurality of stainless steel female snaps 53 which engage and reversibly lock to the male snaps 52. The patient collar 16 is preferably formed of a material sold under the trademark "Gore-Tex" available from W. L. Gore and Associates. This material is suitable to withstand the rigors of the above sterilization procedures noted for the hood 14. Additionally however, they are flexible and are compatible for skin contact with a patient.

Figure 3:
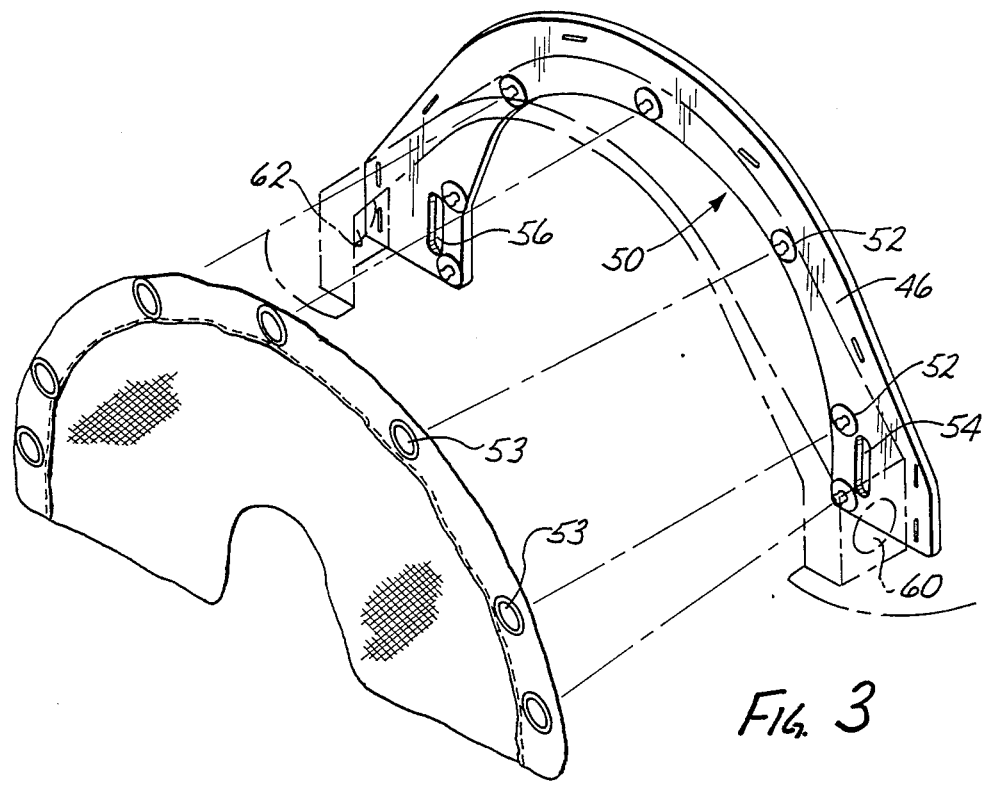
FIG. 3 is an isometric view of certain components of the invention located on the left hand side of FIG. 2.

As is evident from FIG. 2, once the insert 46 is sonic welded to the remainder of the hood 14, the arch baffle 38 projects outwardly from the insert 46 with the flange 42 of the air baffle 38 projecting inwardly toward the patient opening 50 as seen in FIG. 3. With the hood 14 placed over the patient 12 the patient collar 16 is allowed to drape over the patient and contact, as for instance, the neck of the patient to form a gas seal which, while not perfectly gas tight, is a passive seal which tends to inhibit the gas flow adjacent to the body surface of the patient from the interior of the hood to the exterior.

Located on the left and right bottom edges of the insert 46 just outboard of the patient opening 50 are right and left gas outlets 54 and 56 respectively. The gas outlets 54 and 56 are positioned between the patient opening 50 and the arch baffle 38. Further, the gas outlet openings 54 and 56 are open to the ambient air. This is very important with respect to operation of the device. Gas introduced within the interior of the hood 14 via the gas inlet port 44 is freely discharged from the interior of the hood 44 through the outlets 54 and 56 to the ambient air. Gas flow through the hood 14 is therefore governed only by gas pressure at the inlet port 44.

The volume of gas discharged via the gas inlets 54 and 56 exactly equals volume of gas input to the hood 14 via the gas inlet port 44. Any fluctuation of the input flow rate via the inlet port 44 is automatically compensated by the gas outlet flow at the outlet orifices 54 and 56.

Contrary to other prior attempts to scavenge exit gasses from respiratory hoods or tents there is no negative pressure at the gas outlet orifices 54 and 56. Flow rates between the outlet orifices 54 and 56 and the inlet port 44 never have to be equalized, adjusted or compensated for. The scavenging medical hood 10 of the invention is therefore self regulating. Operation personnel need only to set the flow rate of the inlet gas at the inlet port 44 in the manner they would normally use for a typical oxygen tent or oxygen hood.

Since the outlet orifices 54 and 56 are completely open to the ambient atmosphere external to the hood and are unencumbered in exhausting to the ambient atmosphere, they form an obstruction free gas passage between the interior of the enclosure and the ambient air exterior to the enclosure.

Further, the gas outlet orifices 54 and 56 also serve as safety orifices for allowing for introduction of respiratory air to the interior of the hood 14 should the flow of respiratory gasses via the conduit 22 be blocked or in any other way be inhibited. Thus, having the gas outlet orifices 54 and 56 open to ambient air at ambient air pressure additionally serves as a further safety measure for the scavenging medical hood 10 of the invention.

The hood 10 rests on a suitable surface, as for instance, crib surface 58 of FIG. 1, to seal the open bottom side 34 of the hood 14. Before positioning of the device 10 over a patient the patient opening 50 is contiguous with the open bottom of this hood. Positioning of the hood 14 over a patient resting on the surface 58 concurrently essentially seals the hood to the surface 58 and the patient.

The seal formed between the bottom flange 36 and the surface 58 in conjunction with the seal between the collar 16 and the patient 12 is suitably formed simply and maintained by the pressure exerted by the mass of the hood 14 and the adherence of the collar 16 to the neck and/or trunk of the patient 12. Since the gas outlet orifices 54 and 56 are completely open to atmospheric pressure little or no gas and aerosolized medicinal agent contained therein will escape around the bottom flange 36 or the patient collar 16. The path of least resistance formed by directly venting the gas outlet orifices 54 and 56 to the ambient air therefore further insures that residual aerosolized medicinal agent contained within the gas introduced into the hood 14 will exit via the gas outlet orifices 54 and 56 and will not be forced under pressure underneath the bottom flange 36 or around the seal of the collar 16 to the patient 12.

Located just external of and at a right angle to the right and left outlet orifices 54 and 56 are right and left vacuum ports 60 and 62. Each of the vacuum ports 60 and 62 includes a vacuum orifice collectively identified by the numeral 64 as, for instance seen in FIG. 2. The vacuum tubing 18 is split via a tee joint 66 such that it connects to both of the vacuum ports 60 and 62. From the tubing tee 66 the vacuum tubing 18 leads to the vacuum and filter unit 20.

Figure 4:
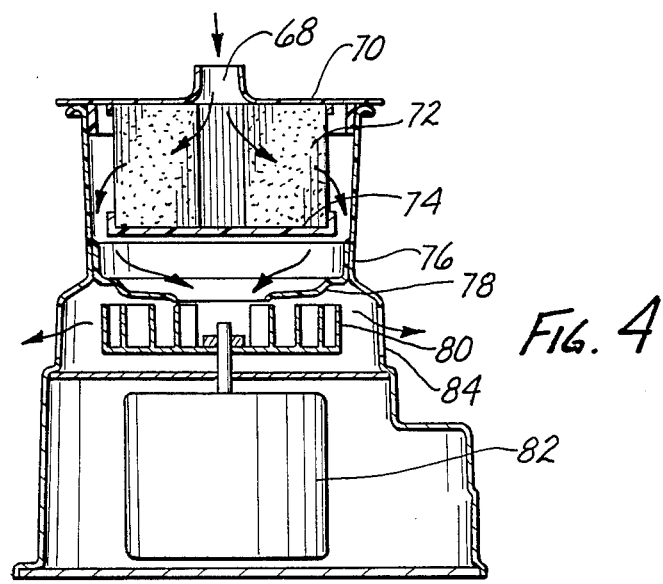
FIG. 4 is an elevational view in section of the filter unit of the invention which is shown in the forefront of FIG. 1.
Figure 5:
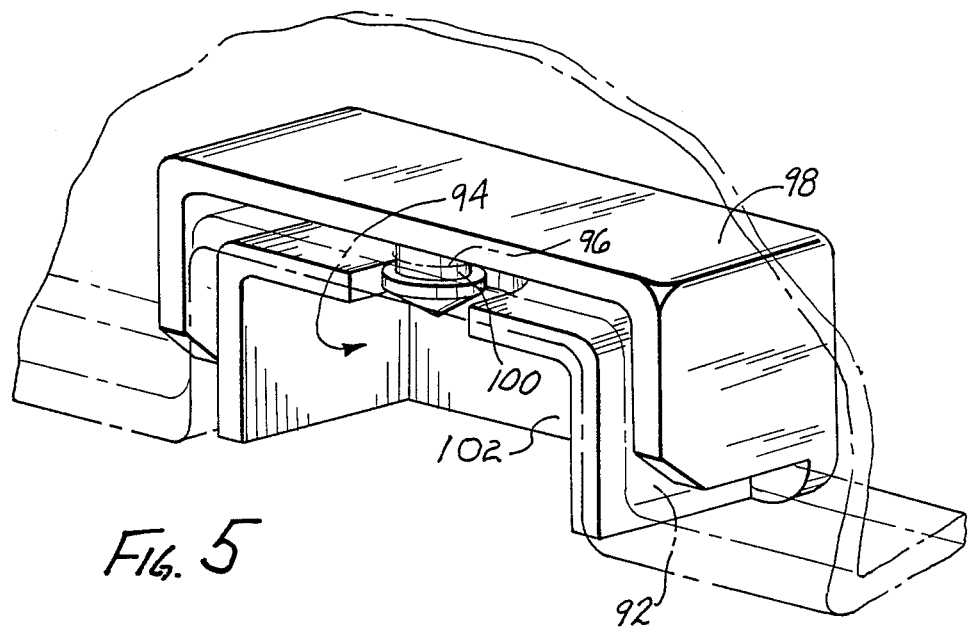
FIG. 5 is an isometric view in partial section of an "auxiliary device through port" located in the circled fragment identified by the numeral 5 of FIG. 2.
Figure 6:
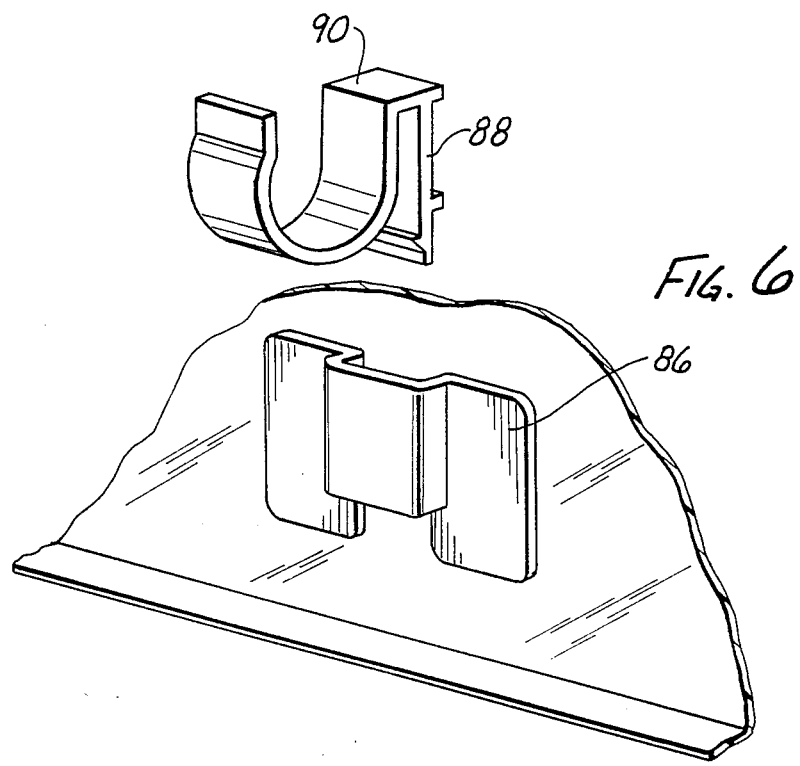
FIG. 6 is an isometric view of a clip for retaining fluid hoses in a confined position adjacent to the hood component of the scavenging medical hood device of the invention as seen in FIG. 1.

As seen in FIG. 4 the vacuum and filter unit 20 includes an input port 68 integrally formed as part of a top 70 of a filter unit 72. The filter unit 72 is formed from a glass fiber which is fan folded in radially extending flutes forming a multi pointed star pattern. This is connected using an appropriate glue to the top 70 as well as to a filter bottom plate 74.

The filter 72 rests inside the outer housing 76 of the vacuum unit directly over an interior baffle 78 having an opening in its center. The opening in the baffle 78 is directly over a vacuum impeller 80 connected to electric motor 82. Operation of the electric motor spins the impeller 80 creating a vacuum in the opening within the baffle 78. This vacuum in turn pulls gas through the filter unit 72 from the input port 68. Vacuum is thus created at input port 68 which is transferred via the tubing 18 to the vacuum ports 60 and 62 on the hood 14.

Upon application of vacuum to the orifices 64 in the vacuum ports 60 and 62 they draw or aspirate gas in to them. Since these orifices are located in direct association with the gas outlet orifices 54 and 56 leading to the interior of the hood 44 and are oriented at an angle to the gas outlet orifices 54 and 56, any gas and residual aerosolized medicinal agent contained therein which is expelled out of the gas outlet orifices 54 and 56 is aspirated into the gas flow flowing into the gas ports 60 and 62. From there any residual aerosolized medicinal agent is conducted downstream to the vacuum filter 72.

The vacuum ports 60 and 62 like the gas outlet orifices 54 and 56 are open to the ambient air. Because of this ambient air is incorporated into the aspirate gas which is aspirated into the vacuum ports 60 and 62 along with exhaust gas from the outlet orifices 54 and 56 and any residual medicinal agent located therein.

The volume of flow of gas aspirated through the vacuum unit 20 is selected to be greater than the volume of flow of respiratory gas introduced via the conduit 22 and the inlet port 44 to the interior of the hood 14. This insures that a sufficient volume of gas is aspirated into the vacuum filter unit 20 which exceeds any volume of gas which is exited to the ambient at the gas outlet orifices 54 and 56.

Typically the volume of gas aspirated into the vacuum and filter unit 20 would be a large multiple of the volume of gas which is output at the gas outlet orifices 54 and 56. For a scavenging medical unit 10 for use with infants as is shown in FIG. 1 the volume of the aspirated gas vacuumed through the filter 72 would be selected to be at least ten times greater, preferably 12 to 15 times greater, than the volume of gas introduced into the hood 14 and thus discharged out of the gas outlet orifices 54 and 56.

Typically medical personnel may adjust the gas flow at the inlet port 44 of the device 10 to be about 15 liters per minute. Use of a 185 liters per minute vacuum and filter unit 20 would thus insure at least 12 volumes of ambient air would be aspirated across the gas inlet orifices 54 and 56 to each volume of outlet gas which is expelled from the gas orifices 54 and 56. This insures that all gas and any residual medicinal agent contained therein which is expelled out of the gas outlet orifices 54 and 56 is incorporated into the gas stream which is aspirated through the filter 72.

Typically medicinal agents are nebulized into suitable gas such that particle sizes of about 1 to 2 microns of the medicinal agent are suspended in the respiratory gas. Gas filter elements suitable for the filter 72 are commercially available which are designed for filtering particles sizes of from 0.5 microns to 20 microns. Such a filter is thus easily suitable for filtration of residual medicinal agent in particle sizes typically output by a typical commercial nebulizer.

As particles are swept through the filter 22 they impact on the glass fibers of the filter impaling themselves thereon and thus are removed from the gas stream which is aspirated through the filter. Gas exhausted at exhaust ports 84 of the filter 20 has thus been cleansed of any residual medicinal agent which was expelled from the hood 14 via the outlet orifices 54 and 56. The filter is fabricated of disposable material. Residual medicinal agent collected on the filter is conveniently and safely disposed of with the filter.

Since there is an overwhelming ratio of the aspirate gas flow through the vacuum and filter unit 20 compared to the outlet at the outlet orifices 54 and 56, medical personnel are free to choose a variety of flow rates for respiratory gasses introduced into the interior of the hood 14 while still maintaining a high degree of safety and insure that any residual medicinal agent not utilized by the patient withfh the hood 14 is safely removed from the exhaust respiratory gasses which are aspirated at the outlet orifices 54 and 56.

Other filtering membranes, as for instance, a HEPA filter medium could be used for the medium for the filter 72 if desired. However, for purging of aerosolized medicinal agents a typical commercial glass filter is normally sufficient in removing such agents from the gas stream aspirated through the filter.

FIG. 6 shows a clip which is utilized to maintain the two arms of the tubing 18 adjacent to the sides 26 and 28 of the hood 14 during operation of the device 10. A U shaped bracket 86 is sonic welded to the side panels 26 and 28 of the hood 14. The bracket 86 is sized and shaped to accept a locking arm 88 of clip 90. The locking arm 88 fits within the bracket 86 to fix the clip 90 to the hood 14. The tubing 18 can then be wedged under slight pressure into the clip 90 to maintain the tube 18 neatly tucked to the sides of the hood 14.

FIG. 5 illustrates a port through the walls of the hood 14 allowing for the introduction of tubes, wires and the like of other medical devices which might be desirable to use inside the hood 14 Such devices might be oxygen and carbon dioxide concentration probes, temperature probes and the like.

A square sided raised section 92 is formed in the bottom flange 36 on both the left and right side of the hood 14. The material corresponding to the left and right sides 26 and 28 is absent in the center of the raised sections 92. This forms two tunnels generally indicated by the numeral 94 through the bottoms of the right and left sides 26 and 28. A small opening 96 is formed on the top of the raised section 92.

A silicone rubber sleeve 98 having a detent 100 on its bottom center fits over the raised section 92 with the detent 100 locking into the opening 96. The back wall 102 of the sleeve 98 seals the tunnel 94 against ingress or egress of gas whether it be respiratory gas out of the device 10 or ambient air into the device 10.

The sleeve 98 is formed of a material as, for instance, a very flexible silicone rubber allowing it to deform slightly to allow for positioning of tubes, wires or the like through the tunnels 94. The back wall 102 of the sleeve 98 deforms over such tubes or wires, however, this deformation is limited to simply that sufficient to allow for passage of the tube or wire through the tunnel 94. Alternately, the user of the hood 10 can cut a slit in the wall 102 and pass the tube or wire through the slit.

Since the hood 14 rests over the patient on the surface 58 it can easily be placed over or removed from the patient by simply lifting up of the same. It is preferable, at least for infants, to size the hood 14 such that it fits over the head, neck and possibly portions of the upper trunk of the patient. This allows for easy access to the lower trunk area of the patient for diaper changing and the like.

The scavenging medical hood 10 of the invention is distinguished from prior known devices since all gasses from the interior of the hood 14 are expelled only to the ambient air and driven only by the pressure differential between the gas inlet pressure and the ambient pressure. In the device 10 no direct vacuum linkages to the interior of the hood 14 are necessary and consequently no adjustment of vacuum gas flows nor equalization of gas flows need be effected by the medical personnel utilizing the scavenging medical hood 10 of the invention.

Further, when aerosolized medication is not being delivered the scavenging hood 10 of the invention can be utilized as a conventional oxygen delivery hood. In such instance it may or may not be desirable to concurrently utilize the vacuum and filter unit 20.

When the vacuum and filter unit 20 are being utilized to scavenge residual aerosolized medicinal agent, the air baffle 38 serves to passivate air currents in the ambient air proximal to both the gas outlet orifices 54 and 56 and the patient opening 50. This increases the efficiency of aspiration of residual aerosolized medicinal agent contained in the gas discharged from the outlet orifices 54 and 56 or around an imperfect seal formed between the collar 16 and the patient 12.

By locating the vacuum ports 60 and 62 at an angle to the outlet orifices 54 and 56 aspirate efficiency is achieved. Thus the flow of gas aspirated into the vacuum ports 60 and 62 is specifically drawn across the surfaces of the gas outlet orifices 54 and 56 to insure that all gas and any residual medicinal agent contained therein expelled from the hood 14 through the outlet orifices 54 and 56 is incorporated into the aspirate gas aspirated into the vacuum and filter unit 20.

I claim:

1. A scavenging medical hood comprising:
   patient enclosure means for enclosing at least the head area of a patient, said patient enclosure means having a hollow interior, said patient enclosure means sized and shaped to contain within said hollow interior at least said head of said patient and a volume of gas suitable for providing respiratory gas to said patient;
   gas inlet port means connecting to said enclosure means for supplying a respiratory gas and an aerosolized medicinal agent contained therein to said interior of said enclosure means;
   gas outlet means connected to said enclosure means for exhausting gas and residual aerosolized medicinal agent from said interior of said enclosure means;
   vacuum port means for aspiration, said vacuum port means located external of said enclosure means in operative association with said gas outlet means for aspirating gas, residual aerosolized medicinal agent and ambient air from the vicinity of said gas outlet means; and
   vacuum means for supplying aspirate vacuum to said vacuum port means.

2. A scavenging medical hood of claim 1 wherein:
   said patient enclosure means includes a hood means for fitting against a surface to define an enclosure having a patient opening, said patient opening sized and shaped to fit around at least the neck region of said patient.

3. A scavenging medical hood of claim 1 wherein:
   said patient enclosure means includes a patient collar means, said collar means for passively sealing against a body surface of said patient to inhibit gas flow adjacent to said body surface from said interior of said enclosure means to the external of said enclosure.

4. A scavenging medical hood of claim 1 wherein:
   said patient enclosure means includes a hood means and a collar means;
   said hood means for fitting against a surface to define an enclosure having a patient opening, said patient opening sized and shaped to fit around at least the neck region of said patient;
   said collar means for passively sealing against a body surface of said patient to inhibit gas flow adjacent to said body surface from said interior of said enclosure means to the external of said enclosure; and
   said collar means attaching to said hood means about said patient opening.

5. A scavenging medical hood of claim 2 wherein:
   said hood means includes a multi-sided hood, one of said sides of said hood being an open bottom side, said open bottom side fitting against said surface; and
   a further of said sides of said hood extending from said open bottom side and including said patient opening, said patient opening contiguous with said open bottom side.

6. A scavenging medical hood of claim 5 wherein:
   said hood is formed of a transparent steam-autoclaveable material.

7. A scavenging medical hood of claim 6 wherein:
   said material is polysulfone.

8. A scavenging medical hood of claim 1 further including:
   air baffle means for passivating ambient air movement, said air baffle means located on and extending from said enclosure means in operative association with both of said gas outlet means and said vacuum port means and at least partially shielding said gas outlet port means and said vacuum port means from air currents in the ambient air.

9. A scavenging medical hood of claim 8 wherein:
   said air baffle means includes an extension element extending from said enclosure means, said extension element having a periphery distal from said enclosure means; and
   said air baffle means further includes a flange extending from at least a portion of said periphery of said extension element.

10. A scavenging medical hood of claim 9 wherein:
    said vacuum port means is positioned on said extension between said flange and said enclosure means; and
    said gas outlet means is positioned on said enclosure means proximal to said extension.

11. A scavenging medical hood of claim 1 wherein:
    said gas outlet means includes at least one gas outlet orifice, said gas outlet orifice extending through said enclosure means between said interior of said enclosure means and the exterior of said enclosure means to form an obstruction free gas passageway between said interior of said enclosure and ambient air exterior of said enclosure.

12. A scavenging medical hood of claim 11 wherein:
    said vacuum port means includes at least one vacuum port orifice, said vacuum port orifice located adjacent to but not contiguous with said gas outlet orifice and at an angle to said gas outlet orifice whereby said gas outlet orifice is open to the ambient air however gas and residual medicinal agent located in said gas which are discharged from said gas outlet orifice are aspirated into said vacuum port orifice.

13. A scavenging medical hood of claim 10 wherein:
    said gas outlet means includes at least one gas outlet orifice, said gas outlet orifice extending through said enclosure means between said interior of said enclosure means and the exterior of said enclosure means to form an obstruction free gas passageway between said interior of said enclosure and ambient air exterior of said enclosure; and
    said vacuum port means includes at least one vacuum port orifice located in said extension element between said flange and said enclosure means adjacent to but not contiguous with said gas outlet orifice and at an angle to said gas outlet orifice whereby said gas outlet orifice is open to the ambient air however gas and residual aerosolized medicinal agent located in said gas which are discharged from said gas outlet orifice are aspirated into said vacuum port orifice.

14. A scavenging medical hood of claim 13 wherein:
    said patient enclosure means includes a multi-sided hood,
    said extension element located on one of the sides of said multi-sided hood;

a patient opening located in said one of the sides of said hood in association with said extension element;

further including two of said gas outlet orifices, each of said gas outlet orifices positioned in said one of the sides of said hood wherein said patient opening is located, one of said gas outlet orifices located on one side of said patient opening and the other of said gas outlet orifices located on the other side of said patient opening; and further including two of said vacuum port orifices positioned opposed to one another in said extension element on opposite sides of said patient opening, one of said vacuum port orifices adjacent one of said gas outlet orifices and the other of said vacuum port orifices adjacent the other of said gas outlet orifices.

15. A scavenging medical hood of claim 1 wherein:
said vacuum means includes a motorized vacuum source and a filter, said filter positioned between said motorized vacuum source and said vacuum port means for filtering said residual aerosolized medicinal agent from aspirate aspirated into said vacuum port means.

16. A scavenging medical hood comprising:
a multi-sided hood having a hollow interior;
a gas inlet port located in one of the sides of said hood;
a patient opening located in one of the sides of said hood;
at least one gas outlet orifice located in one of the sides of said hood and extending between the interior of said hood and ambient air exterior of said hood;
at least one vacuum port having a vacuum orifice positioned adjacent to said gas outlet orifice whereby in response to gas movement through said vacuum orifice gas is aspirated from the ambient air area immediately adjacent said gas outlet orifice; and
a motorized vacuum source and a filter, said vacuum source connected to said vacuum port for aspirating gas into said vacuum orifice, said filter positioned in said aspirated gas downstream from said vacuum orifice.

17. A scavenging medical hood of claim 16 including:
an air baffle located on said same one of the sides of said hood wherein said patient opening is located, said air baffle at least partially surrounding said patient opening;
said gas outlet further located on said same one of the sides of said hood wherein said patient opening is located and positioned on said side between said patient opening and said air baffle; and
said vacuum port including said vacuum orifice located on said air baffle at an angle with respect to said gas outlet orifice.

18. A scavenging medical hood of claim 17 including:
two of said gas outlet orifices and two of said vacuum orifices;
each of said gas outlet orifices located on said same one of the sides of said hood wherein said patient opening is located, each of said gas outlet orifices located between said patient opening and said air baffle;
one of said gas outlet orifices located on one side of said patient opening and the other of said gas outlet orifices located on the other side of said patient opening;
each of said vacuum orifices located on said air baffle; and
one of said vacuum orifices located adjacent to one of said gas outlet orifices and the other of said vacuum orifices located adjacent to the other of said gas outlet orifices.

19. A scavenging medical hood of claim 16 including:
one of said sides of said hood being an open side forming the bottom of said hood, said open bottom positionable against a surface to essentially seal said hood to said surface against gas flow from said open bottom of said hood.

20. A scavenging medical hood of claim 16 wherein:
said hood is formed of a transparent steam-autoclaveable material.

21. A scavenging medical hood of claim 16 wherein:
said hood is formed of polysulfone material.

22. A medical scavenging hood of claim 17 wherein:
said air baffle includes an arch shaped extension element extending from said side of said hood wherein said patient opening is located, said arch shaped extension extending over said patient opening, said extension element having a periphery distal from said hood;
said air baffle further including a flange extending from said periphery of said extension element, said flange oriented towards said patient opening.

23. A scavenging medical hood of claim 16 including:
a patient collar attaching to said side of said hood wherein said patent opening is located and positioned around a portion of said patient opening, said patient collar passively sealing against a body surface of said patient to inhibit gas flow adjacent to said body surface from said interior of said hood to the external of said hood.

* * * * *